United States Patent [19]

Roques et al.

[11] Patent Number: 4,513,009
[45] Date of Patent: Apr. 23, 1985

[54] AMINOACID DERIVATIVES AND THEIR THERAPEUTIC APPLICATIONS

[75] Inventors: Bernard Roques, Saint Maurice; Jean-Charles Schwartz; Jeanne-Marie Lecomte, both of Paris, all of France

[73] Assignee: Societe Civile Bioprojet, Paris, France

[21] Appl. No.: 254,208

[22] Filed: Apr. 14, 1981

[30] Foreign Application Priority Data

Apr. 17, 1980 [FR] France ................ 80 08601

[51] Int. Cl.³ ............. A01N 37/12; A01N 37/10; C07C 153/00
[52] U.S. Cl. ................ 514/513; 260/455 R; 514/618
[58] Field of Search .............. 424/309, 319; 260/455 R

[56] References Cited

U.S. PATENT DOCUMENTS

| | | | |
|---|---|---|---|
| 4,053,651 | 10/1977 | Ondetti et al. | 424/319 |
| 4,105,789 | 8/1978 | Ondetti et al. | 424/309 |
| 4,108,886 | 8/1978 | Ondetti | 260/455 R |
| 4,228,184 | 10/1980 | Ondetti et al. | 424/309 |
| 4,256,761 | 3/1981 | Suh et al. | 260/455 R |
| 4,328,242 | 5/1982 | De Vincentiis | 260/455 R |

FOREIGN PATENT DOCUMENTS

| | | | |
|---|---|---|---|
| 0009898 | 4/1980 | European Pat. Off. | 260/112.5 R |
| 0012401 | 6/1980 | European Pat. Off. | 260/112.5 R |
| 0036713 | 9/1981 | European Pat. Off. | 260/112.5 R |
| 0038046 | 10/1981 | European Pat. Off. | 260/112.5 R |
| 0048159 | 3/1982 | European Pat. Off. | 260/112.5 R |
| 0068739 | 1/1983 | European Pat. Off. | 260/112.5 R |

*Primary Examiner*—Delbert R. Phillips
*Attorney, Agent, or Firm*—Young & Thompson

[57] ABSTRACT

This invention relates to aminoacid derivatives, and compositions containing the same and having enkephalinase-inhibiting, antalgic, antidiarrhea and hypotensive activities, of the formula

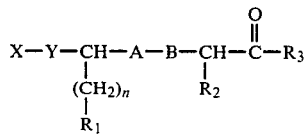

whose variables are as set forth herein, for example

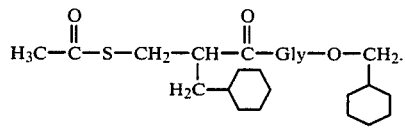

17 Claims, No Drawings

AMINOACID DERIVATIVES AND THEIR THERAPEUTIC APPLICATIONS

This invention relates to new aminoacid derivatives and to therapeutic compositions containing the same.

The derivatives of this invention are inhibitors of enkephalinase which is an enkephalin-degrading enzyme.

Methionine-enkephalin, Met-E (Tyr-gly-gly-Phe-Met) and leucine-enkephalin, Leu-E(Tyr-gly-gly-Phe-Leu) are peptides discovered in the brain and which are the endogenic ligands of the morphinic receptor (J. Hughes et al., Nature 258, 577 (1975)).

They have a multiple action, both at the level of the transmission of nociceptive influx and at the level of behavior or hormonal secretion. They are considered as being neuromediators having an inhibitory action on the action of other neurotransmittors [J. Hughes, Nature 278, 394 (1979); S. H. Snyder, Nature, 278, 13 (1979)]. It has been demonstrated that enkephalins are rapidly degraded in the brain by a carboxydipeptidase which liberates the Tyr-gly-gly and Phe-Met residues (B. Malfroy et al, Nature 276, 523 (1978).

The compounds capable of inhibiting enkephalinase are thus able to extend the effects of endogenic enkephalins or to potentiate the action of synthetic analogs administered in an exogenous manner. Thus, said compounds may replace morphinic agents in all their properties without exhibiting the serious drawbacks of the latter, particularly at the level of habit-forming and dependence phenomena.

The derivatives of this invention have the general formula:

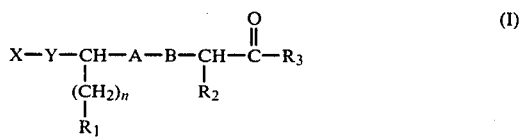

(I)

in which:

A is a group selected from the carbonyl, methylene, and amino groups;

B is selected from an amino group; an amino group substituted with a $C_{1-4}$ alkyl group; a carbonyl group, and a thio group;

$R_1$ is selected from: a hydrogen atom; an alkyl group; an alkyl group monosubstituted with a halogen atom; an alkyl group polysubstituted with halogen atoms; a phenyl group; a phenyl group monosubstituted with a substituent selected from halogen, trifluoromethyl and hydroxy; a phenyl group polysubstituted with substituents selected from halogen, trifluoromethyl and hydroxy; a cyclohexyl group; and a thienyl group;

n is selected from 0 and 1;

$R_2$ is selected from: hydrogen; straight-chain $C_{1-6}$ alkyl; branched-chain $C_{1-6}$ alkyl; phenyl; benzyl; benzyl mono-halosubstituted; benzyl poly-halosubstituted; hydroxyalkyl; alkoxyalkyl; alkoxyalkyl substituted on the alkoxy moiety with a substituent selected from phenyl, benzhydryl, pyridyl N-substituted with a phenyl alkyl group, and pyridyl N-substituted with a phenylalkyl group whose phenyl nucleus is mono- or poly-halosubstituted; phenoxyalkyl; mercaptoalkyl; mercaptoalkyl substituted at the sulfur atom with a substituent selected from straight and branched-chain alkyl, phenyl and benzyl;

$R_3$ is a group selected from the $OR_4$, $NHR_4$ and $N(R_4)_2$ groups in which $R_4$ is selected from: hydrogen; $C_{1-8}$ straight- and branched chain alkyl; $C_{1-8}$ straight and branched chain alkyl mono- or poly-halosubstituted; phenyl; phenyl mono- or poly-halosubstituted; phenyl$C_{1-8}$alkyl; phenyl($C_{1-8}$alkyl) mono- or polyhalosubstituted on the phenyl nucleus; dialkylamino- and dialkylaminoxyalkyl in which the alkyl groups contain 1–4 carbon atoms;

Y is selected from: —S—; —NH—; —$CH_2$—; and tertiary amino whose third valency forms with $R_1$ an alkylene bridge having 2 carbon atoms; and X is selected from: hydrogen; $C_{1-2}$alkyl substituted with a substituent selected from alkoxycarbonyl, carboxy, mercapto, alkylthio, alkylthio mono- or poly-halosubstituted, benzylthio, benzylthio mono- or polysubstituted with a substituent selected from halogen and mono- or poly-$C_{1-4}$alkyl, benzhydrylthio, benzhydrylthio mono- or polyhalosubstituted, aliphatic $C_{1-4}$acyl thio, aliphatic $C_{1-4}$acyl thio mono- or poly-halosubstituted, benzoylthio, benzoylthio mono- or poly-substituted with a substituent selected from halogen and $C_{1-4}$mono- or polyhalo-alkyl, benzylcarbonylthio, benzylcarbonylthio mono- or poly-halosubstituted on the phenyl nucleus, benzhydrylcarbonylthio, and benzhydrylcarbonylthio mono- or poly-halosubstituted on the phenyl nucleus; $C_{1-4}$ aliphatic acyl; benzoyl; alkoxycarbonyl; mercapto; aliphatic $C_{1-4}$acyl thio; benzoylthio; phenyl($C_{1-4}$alkyl) carbonylthio; phenyl($C_{1-4}$alkyl)carbonylthio mono- or polyhalosubstituted; hydroxy($C_{1-4}$alkyl)carbonylthio; and amino($C_{1-4}$alkyl)carbonylthio;

and their addition salts with pharmaceutically acceptable acids and bases, provided that there are not simultaneously $X=R_1=R_2=H$, $Y=CH_2$ and $n=0$.

Among the above-defined compounds of the formula (I), a preferred class of compounds comprises the derivatives in which:

A is a group selected from carbonyl, methylene and amino;

B is a group selected from amino, carbonyl and thio;

$R_1$ is selected from: hydrogen; phenyl; and phenyl mono- or polyhalosubstituted;

n is selected from 0 and 1;

$R_2$ is selected from hydrogen; straight- and branched $C_{1-6}$ alkyl; benzyl; and benzyloxyalkyl;

$R_3$ is selected from the —$OR_4$, —$NHR_4$ and —$N(R_4)_2$ groups in which $R_4$ is selected from: hydrogen; straight- and branched $C_{1-6}$ alkyl; straight- and branched $C_{1-6}$ alkyl mono- or poly-halosubstituted; phenyl; phenyl mono- or polyhalosubstituted; phenyl($C_{1-4}$alkyl); phenyl($C_{1-4}$alkyl) mono- or polyhalosubstituted on the phenyl nucleus; dialkyl aminoalkyl in which the alkyl groups contain 1–4 carbon atoms; and dialkylaminoxyalkyl in which the alkyl groups contain 1–4 carbon atoms;

Y is selected from —S—; —NH—, —$CH_2$—, and tertiary amino in which the third valency forms with $R_1$ an alkylene bridge containing 2 carbon atoms;

X is selected from: hydrogen; $C_{1-2}$ alkyl substituted with a substituent selected from alkoxycarbonyl, carboxy, mercapto, aliphatic $C_{1-4}$acylthio, and benzoyl thio; aliphatic $C_{1-4}$acyl; benzoyl; $C_{1-4}$alkoxycarbonyl; mercapto; aliphatic $C_{1-4}$acylthio; benzoylthio; phenyl($C_{1-4}$alkyl)carbonylthio; phenyl($C_{1-4}$alkyl)carbonylthio mono- or polyhalosubstituted; hydroxy($C_{1-4}$alkyl)carbonylthio; and amino($C_{1-4}$alkyl)carbonylthio.

Fluorine is the preferred halogen atom. Examples of useful aliphatic acyl groups include the acetyl, propionyl and butyryl groups, the preferred group being the acetyl group.

Among the compounds of the formula (I) are preferred those having the following aminoacid structures: leucine, phenylalanine, glycine, serine and alanine.

Specific compounds contemplated by this invention are the following derivatives (in the following formulae Et=ethyl and $\phi$=a phenyl group):

| | |
|---|---|
| $EtO_2C-CH_2-L\text{-Phe}-L\text{-Leu}-OCH_3$ | (1) |
| $HO_2C-CH_2-L\text{-Phe}-L\text{-Leu OH}$ | (2) |
| $HO_2C-CH_2-L\text{-Phe}-(CH_3)-L\text{-Leu OH}$ | (3) |
| $HO_2C-CH_2-L\text{-Phe}-D\text{ Leu OH}$ | (4) |
| $HO_2C-CH_2-D\text{-Phe}-L\text{-Leu OH}$ | (5) |
| $HO_2C-CH_2-D\text{-Phe}-D\text{-Leu OH}$ | (6) |
| $EtO_2C-CH_2-CH_2-L\text{-Phe}-L\text{-Leu OCH}_3$ | (7) |
| $HO_2C-CH_2-CH_2-L\text{-Phe}-L\text{-Leu OH}$ | (8) |
| $EtO_2C-CH_2-L\text{-Phe}-L\text{.Ala}-OCH_3$ | (9) |
| $HO_2C-CH_2-L\text{-Phe}-L\text{.Ala}-OH$ | (10) |
| $HS-CH_2-CH_2-L\text{-Phe Otbu}$ | (11) |
| $\phi\text{-COS}-CH_2-CH_2-L\text{.Phe Otbu}$ | (12) |
| $\phi\text{-COS}-CH_2-CH_2-L\text{.Phe OH}$ | (13) |
| $\phi\text{-COS}-CH_2-CH_2-L\text{-Phe}-L\text{-Leu OCH}_3$ | (14) |
| $HS-CH_2-CH_2-L\text{-Phe}-L\text{-Leu OH}$ | (15) |
| $HS-CH_2-CH_2-L\text{-Phe}-L\text{-Ala OH}$ | (16) |

(17) $CH_3-COS-CH_2-\underset{\underset{CH_2-\phi}{|}}{CH}-CO-L\text{-Leu OCH}_3$ (R,S and S,S)

(18) $HS-CH_2-\underset{\underset{CH_2-\phi}{|}}{CH}-CO-L\text{-Leu OH}$ (R,S and S,S)

(19) $CH_3-COS-CH_2-\underset{\underset{CH_2-\phi}{|}}{CH}-CO-\text{Gly OCH}_3$ (R and S)

(20) $HSCH_2-\underset{\underset{CH_2-\phi}{|}}{CH}-CO-\text{Gly OH}$ (R and S)

(21) $CH_3-COS-CH_2-\underset{\underset{CH_2-\phi}{|}}{CH}-CO-L\text{.Ala OCH}_3$ (R,S and S,S)

(22) $HS-CH_2-\underset{\underset{CH_2-\phi}{|}}{CH}-CO-L\text{-Ala OH}$ (R,S and S,S)

(23) $\phi\text{-COS}-CH_2-\underset{\underset{CH_2-\phi}{|}}{CH}-CO-L\text{-Ser OCH}_3\ (OCH_2-\phi)$ (R,S and S,S)

(24) $HS-CH_2-\underset{\underset{CH_2-\phi}{|}}{CH}-CO-L\text{-Ser OH}\ (OCH_2-\phi)$ (R,S and S,S)

(25) $CH_3-COS-CH_2-\underset{\underset{CH_2-\phi\text{-F}}{|}}{CH}-CO-L\text{-Leu OCH}_3$ (R,S and S,S)

(26) $HS-CH_2-\underset{\underset{CH_2-\phi\text{-F}}{|}}{CH}-CO-L\text{-Leu OH}$ (R,S and S,S)

(27) $\phi\text{-COS}-\underset{\underset{CH_2-\phi}{|}}{CH}-CO-L\text{-Leu OH}$ (S,S)

(28) $HS-\underset{\underset{CH_2-\phi}{|}}{CH}-CO-L\text{-Leu}-OH$ (S,S)

-continued

(29) $CH_3-COS-\underset{\underset{CH_2-\phi}{|}}{CH}-CO-L\text{-Leu OCH}_3$ (S,S)

(30) $HS-\underset{\underset{CH_2-\phi}{|}}{CH}-CO-L\text{-Leu}-OCH_3$ (S,S)

(31) $CH_3-COS-\underset{\underset{CH_2-\phi}{|}}{CH}-CO-L\text{-Leu OH}$ (S,S)

(32) $HS-\underset{\underset{CH_2-\phi}{|}}{CH}-CO-L\text{.Ala OH}$ (S,S)

(33) $CH_3-COS-CH_2S-\underset{\underset{CH_2-\phi}{|}}{CH}-CO-L\text{-Leu}-OH$ (S,S)

(34) $\phi\text{-COS}-CH_2-CH_2-S-\underset{\underset{CH_2-\phi}{|}}{CH}-CO-L\text{-Leu}-OH$ (S,S)

(35) $HS-CH_2-CH_2-S-\underset{\underset{CH_2-\phi}{|}}{CH}-CO-L\text{-Leu}-OH$ (S,S)

(36) $HS-CH_2-CH_2-S-\underset{\underset{CH_2-\phi}{|}}{CH}-CO-L\text{-Ala OH}$ (S,S)

(37) $tboc\text{-NH}-\underset{\underset{CH_2-\phi}{|}}{CH}-NH-CO-\underset{\underset{CH_3}{|}}{CH}-CO_2-Et$ (SR + SS)

(38) $tboc\text{-NH}-\underset{\underset{CH_2-\phi}{|}}{CH}-NH-CO-\underset{\underset{CH_3}{|}}{CH}-CO_2H$ (SR + SS)

(39) $H_2N-\underset{\underset{CH_2-\phi}{|}}{CH}-NH-CO-\underset{\underset{CH_3}{|}}{CH}-CO_2H$ (RR + RS)

(40) $HO_2C-CH_2-NH-\underset{\underset{CH_2-\phi}{|}}{CH}-NH-CO-\underset{\underset{CH_3}{|}}{CH}-CO_2H$ (RR + RS)

(41) $HS-CH_2-CH_2-NH-\underset{\underset{CH_2-\phi}{|}}{CH}-NH-CO-\underset{\underset{CH_3}{|}}{CH}-CO_2H$ (RR + RS)

(42) $tboc\text{-NH}-\underset{\underset{CH_2-\phi}{|}}{CH}-CH_2-S-CH_2-COOH$ (S)

(43) $H_2N-\underset{\underset{CH_2-\phi}{|}}{CH}-CH_2-S-CH_2-COOH$ (S) TFA

(44) $HO_2C-CH_2-NH-\underset{\underset{CH_2-\phi}{|}}{CH}-CH_2-S-CH_2-COOH$ (S)

(45) $HS-CH_2-CH_2-NH-\underset{\underset{CH_2-\phi}{|}}{CH}-CH_2-S-CH_2-CH_2-CO_2H$ (S)

(46) $tboc\text{-NH}-\underset{\underset{CH_2-\phi}{|}}{CH}-CH_2-L\text{-Leu}-OCH_3$ (S,S)

(47) $HO_2C-CH_2-NH-\underset{\underset{CH_2-\phi}{|}}{CH}-CH_2-L\text{-Leu OH}$ (S,S)

$$\text{HS—CH}_2\text{—CH}_2\text{—NH—CH—CH}_2\text{—L-Leu OH (S,S)} \quad (48)$$
$$\text{with CH}_2\text{—}\phi \text{ branch}$$

EtOCOCH$_2$—L-Pro—L-Ala OCH$_3$ (49)
HOOC—CH$_2$—L-Prop—L-Ala OH (50)

$\phi$CH$_2$COSCH$_2$—CH—CO—Gly—OCH$_2\phi$ (R,S) (51)
  |
  CH$_2\phi$ $\phi$COSCH$_2$—CH—CO—Gly OCH$_2\phi$ (R,S) (52)
  |
  CH$_2\phi$ CH$_3$—COSCH$_2$—CH—CO—Gly OCH$_2\phi$ (R,S) (53)
  |
  CH$_2\phi$ CH$_3$—COSCH$_2$—CH—CO—Gly OCH$_2$pF$\phi$ (R,S) (54)
  |
  CH$_2\phi$ CH$_3$—COSCH$_2$—CH—CO—Gly OCH$_2$F$_3$ (R,S) (55)
  |
  CH$_2\phi$ CH$_3$—COSCH$_2$—CH—CO—Gly NHCH$_2\phi$ (R,S) (56)
  |
  CH$_2\phi$ HS CH$_2$—CH—CO—Gly OCH$_2\phi$ (R,S) (57)
  |
  CH$_2\phi$ HS CH$_2$—CH—CO—Gly OCH$_2$pH$\phi$ (R,S) (58)
  |
  CH$_2\phi$ HS CH$_2$—CH—CO—Gly OCH$_2$CF$_3$ (R,S) (59)
  |
  CH$_2\phi$ HS CH$_2$—CH—CO—Gly NHCH$_2\phi$ (R,S) (60)
  |
  CH$_2\phi$ The compounds of the formula (I) have one or two asymmetrical carbon atoms. Thus, they exist as racemic mixtures or as diastereoisomers. All said compounds are included within the scope of the present invention. The syntheses described hereinafter may use the racemate or one of the enantiomers as starting material. When the racemic starting material is used in the synthetic procedure, the stereoisomers obtained in the product may be separated by conventional chromatographic or fractional crystallization methods. Generally, the isomer L with respect to the carbon atom of the aminoacid constitutes the preferred isomeric form.

The compounds of the formula (I) form salts which are also part of this invention. The salts include the acid addition salts formed by reaction with various inorganic and organic acids producing acid addition salts comprising, for example, the hydrohalides (particularly the hydrochloride and the hydrobromide), the sulfate, the nitrate, the borate, the phosphate, the oxalate, the tartrate, the maleate, the citrate, the acetate, the ascorbate, the succinate, the benzenesulfonate, the methanesulfonate, the cyclohexanesulfonate and the toluenesulfonate. The addition salts with bases are formed by reaction with bases such as NaOH or by ion-exchange reaction.

The salts are formed in conventional manner, by reacting the free form of the product with one or more equivalents of the suitable base or acid providing the desired anion or cation, within a solvent or medium in which the salt is insoluble or in water, and by removing the water by lyophilization. Neutralization of the salt with an insoluble acid such as a cation exchange resin in hydrogen form [for example Dowex-50 polystyrenesulfonic acid resin (Mikes, Laboratory Handbook of Chromatographic Methods (Van Nostrand) page 256], elution with a volatile buffer (such as pyridine/acetic acid) and extraction with an organic solvent provides the free form and, if desired, another salt may be formed.

The compounds of this invention may be prepared by the various processes defined hereinafter.

The compounds of the formula (I) may be prepared by conventional peptidic condensation reaction between two suitably protected aminoacid residues.

For example, the functional group(s) (i.e., amino, carboxy, hydroxy) which are not involved in the reaction for the formation of the peptide linkage (i.e., —CONH) during the condensation reaction may be protected with one or more protecting groups prior to the condensation reaction.

Useful intermediate protecting groups of the amino groups include usual groups such as t.butoxycarbonyl (Boc), benzyloxycarbonyl (Z), isobornyloxycarbonyl (IBOC) and the like.

If necessary, the carboxyl groups may also be protected by esterification (for example, methyl, ethyl, benzyl esters, and the like).

The condensation reaction is effected by using preferably the coupling of the nitrides without racemisation, or the dicyclohexyl carbodiimide/1-hydroxy-benzotriazole process referred to hereinafter as DCC/HOBt or DCC/3-hydroxy-4-oxo-3,4-dihydro-1,2,3-benzotriazine (OOBt). As a modification, the activated esters of the fragments may also be used.

The condensation reaction may be effected in the presence of a solvent. The solvent may be selected from those known as being useful in peptide condensation reactions. Thus, examples include the following anhydrous or aqueous solvents: dimethylformamide, dimethylsulfoxide, pyridine, chloroform, dioxan, dichloromethane, tetrahydrofuran, and suitable mixtures thereof.

The reaction temperature is selected from the range known for reactions leading to the formation of peptide linkages, for example, normally, within about −20° C. to about 30° C. In addition, the precursor materials (protected peptides) of the desired compounds of this invention may also be readily prepared by solid phase synthesis procedures.

On completion of the desired condensation reaction, when the product carries protecting groups, these may be removed by usual methods. Such usual methods include: catalytic reduction in the presence of a catalyst such as palladium black, carbon-over-palladium, platinum, etc, solvolysis with hydrofluoric acid, trifluoroacetic acid, etc., and reduction with sodium metal within liquid ammonia.

Trifluoroacetic acid (TFA) is typically used to remove the Boc (amino protecting) groups and a saponification is typically used to remove the protecting ester groups of the carboxyl groups.

The compounds of the formula (I) may also be prepared by condensation between a fraction of a halogenated derivative and the corresponding fraction of an amino or mercapto derivative.

According to a first embodiment, the compounds of the formula (I) in which A=CO, B=NH, Y=NH, X is a $C_1$ or $C_2$ alkylene group substituted with an alkoxycarbonyl or carboxy group and $R_1$, $R_2$, $R_3$ and n are as defined above, are prepared by reacting a derivative of the formula

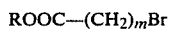  (II)

ROOC—$(CH_2)_m$Br in which R is H or alkyl and m is 1 or 2, with a derivative of the formula

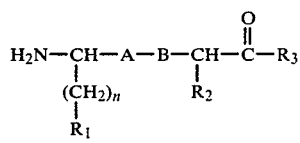  (III)

in which $R_1$, $R_2$ and $R_3$ are as defined above and A=CO; B=NH.

The compounds of the formula (III) are obtained by conventional peptidic synthesis routes, i.e., by coupling of a protected derivative

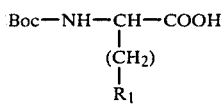

with ester or amide

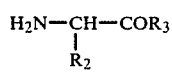

using a variety of previously indicated methods such as HOBT/DCC, mixed anhydride, activated ester. The protecting group Boc is then removed, for example with trifluoroacetic acid (TFA).

According to another embodiment, the compounds of the formula (I) in which A=$CH_2$, B=NH, Y=S, X is hydrogen or benzoyl, $R_1$=H, n=0, $R_2$ and $R_3$ have the above-defined meanings, are prepared:

(a) by reaction of thiiran having the formula $C_2H_4S$ with an aminoacid ester or amide having the formula:

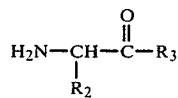  (III)

and (b) optionally by reaction of the product obtained in step a) with a compound having the formula:

R—CO—Br in which R is lower alkyl or phenyl, and removal of the protecting groups.

According to another embodiment of the present invention, the compounds of the formula (I) in which A=CO, B=NH, Y=NH or $CH_2$, X is a $C_1$ or $C_2$ alkyl group substituted with a mercapto, aliphatic acyl thio or benzoylthio group, $R_1$, $R_2$, $R_3$ and n are as defined above are prepared by a peptidic condensation reaction between a compound of the formula:

  (IV)

and an aminoacid ester or amide of the formula

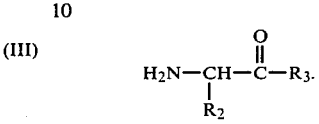

When the compound of the formula (IV) includes a group Y which is a —NH— group, it is prepared as described in the preceding embodiment.

When the compound of the formula (IV) includes a group Y which is a —$CH_2$— group, it is obtained by reaction of a thiocarboxylic S-acid of the formula R—COSH in which R is alkyl, phenyl, or benzyl optionally mono- or poly-halosubstituted, with an acrylic acid derivative of the formula

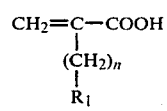

(prepared according to C. Mannich & K. Ritsert, 1924, Ber 57, 1116), to give a compound having the formula:

  (IVa)

According to another embodiment of the present invention, the compounds of the formula (I) in which A=CO, B=NH, Y=S, X is hydrogen or a $C_{1-4}$ aliphatic acyl or benzoyl group, and $R_1$, $R_2$, $R_3$ and n have the above defined meanings, are prepared by reaction of a thiocarboxylic S-acid of the formula R—COSH, in which R is alkyl or phenyl, with a halo derivative of the formula:

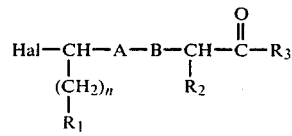  (V)

in which Hal is a halogen atom, particularly bromine.

The compounds of the formula (V) are obtained by a coupling reaction analogous to the peptidic synthesis between a bromoacid of the formula:

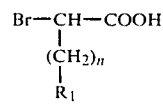

and an aminoacid ester or amide of the formula

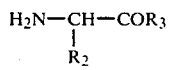

According to a modification of this embodiment, it is possible first to react the bromoacid with the carboxylic S-acid, and then to couple the resulting acid with the amonoacid ester or amide.

According to a further embodiment of the present invention, the compounds of the formula (I) in which A=CO, B=NH, Y=S, X is a $C_1$ or $C_2$ alkyl substituted with a mercapto, aliphatic acyl thio or benzoylthio group and $R_1$, $R_2$, $R_3$ and n have the above-defined meanings, are prepared by reaction of a halogen containing compound of the formula R—CO—S—$(CH_2)_m$—Hal, in which Hal is a halogen atom such as bromine, R is alkyl or phenyl and m is 1 or 2, with a derivative of the formula:

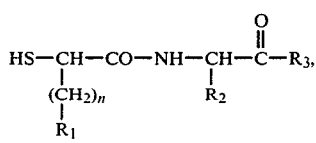

the latter compound being obtained from a compound of the formula (I) whose synthesis has already been described, by removal of the mercapto end group.

The synthesis of the compounds of the formula (I) in which Y=$CH_2$ and X is an aliphatic acylthio group; a phenyl($C_{1-4}$alkyl)carbonylthio group in which the aromatic residue is mono- or poly-halosubstituted; a hydroxyalkylcarbonylthio group or an aminoalkylcarbonylthio group is effected by condensation of the corresponding acid chlorides in the presence of the DDC/HOBT mixture with derivatives (I) in which Y=$CH_2$ and X=SH.

The production of mercapto-terminated derivatives of the formula (I) is effected by saponification with sodium hydroxide of aliphatic or aromatic acyl-thio terminated derivatives. This saponification leads to a predominance of duplication compounds with disulfide linkage, said oxidation reaction occurring in a major amount, even when using degassed solvents and when operating under a protecting nitrogen atmosphere. The mercapto-terminated compounds of the formula (I) are thus obtained pure, by effecting an in situ reduction with nascent hydrogen on completion of the saponification reaction.

The compounds of the formula (I) in which Y=$CH_2$, X=SH, and $R_1$, $R_2$ and $R_3$ are as defined above, are prepared by the following reaction sequence:

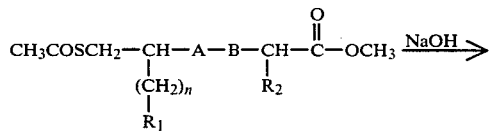

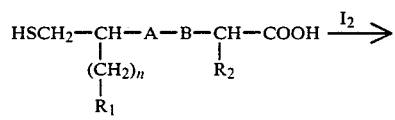

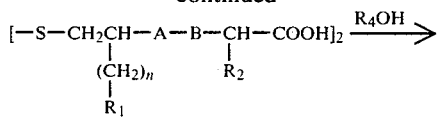

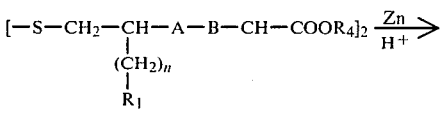

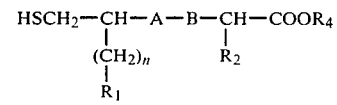

When in general formula (I) the $R_3$ residue is a primary or secondary amine group, direct saponification of the acetylthio derivatives makes it possible to obtain directly derivatives (I) in which X=SH and Y=$CH_2$—.

According to a further embodiment, the compounds of the formula (I) in which A=NH, B=CO, Y=NH, X is selected from hydrogen, carboxy- or mercapto-substituted alkyl, and alkoxycarbonyl, and $R_1$, $R_2$ and $R_3$ have the above-defined meanings, are prepared by a peptidic condensation reaction between a N-protected diamine of the formula

and a malonic monoester or monoamide of the formula:

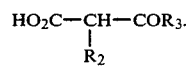

The diamine of the formula (IV) is obtained by a Curtius reaction according to M. Chorev et al. [J. Amer. Chem. Soc., 99, 8075 (1977)] with a N-protected aminoacid, according to the following reaction scheme:

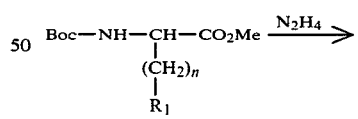

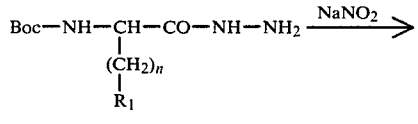

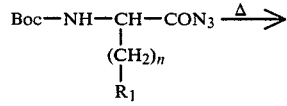

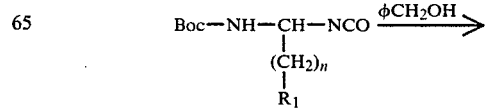

-continued

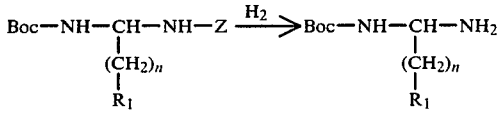

According to another embodiment, the compounds of the formula (I) in which A=CH$_2$; B=S; Y=NH; X is hydrogen, carboxy- or mercapto-substituted alkyl, or alkoxycarbonyl; and R$_1$, R$_2$ and R$_3$ have the above-defined meanings, are prepared by a condensation reaction between a tosylated N-protected aminoacid derivative of the formula:

and a thioglycolic ester or amide having the formula:

according to the method of H. Gilman et al., J. Amer. Chem. Soc., 47, 1449 (1915).

The compounds of the formula (VII) are obtained by reduction with sodium borohydride (according to the method of Seki et al., Chem. Pharm. Bull., 13, 995-VII-1965) of a N-protected aminoacid ester having the formula:

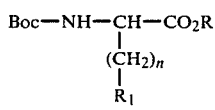

in which R is alkyl, followed by conversion of the resulting alcohol to a tosylated derivative of the formula (VII) by action of p-toluenesulfonic acid.

The compounds of the formula (VIII) are obtained by the method according to E. Fischer et al., Annalen, 357, 1 (1907) or described in DOS No. 2,349,707, according to the following reaction scheme:

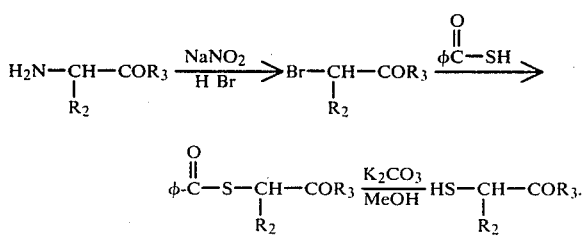

According to another embodiment, the compounds of the formula (I) in which A=—CH$_2$—; B=—NH—; Y=NH; X is selected from hydrogen, carboxy- or mercapto-substituted alkyl, and alkoxycarbonyl; and R$_1$, R$_2$ and R$_3$ have the above-defined meanings, are prepared by a condensation reaction between a tosylated N-protected aminoacid derivative of the above described formula (VII) and an aminoacid ester or amide of the formula:

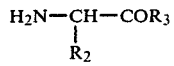

according to the technique of V. C. Sekera et al., J. Amer. Chem. Soc., 55, 345 (1933).

The following non-limiting Examples are given to illustrate the preparation of compounds according to the present invention.

EXAMPLE 1

N-(Ethoxycarbonyl-methyl)-L.phenylalanine-L.leucine methyl ester

Triethylamine (3 ml) is slowly added, in the cold and under a nitrogen atmosphere, to a suspension of dipeptide-ester: L.Phe-L.Leu OCH$_3$ trifluoroacetate (10 g) in anhydrous benzene (50 ml). On completion of the addition, the suspension becomes clear. Ethyl bromoacetate (3.34 g) is then added, and the solution is refluxed for 12 hours. After cooling, 0.25N sodium hydroxide is added dropwise, in an ice-bath, to pH 6.

The aqueous phase is rapidly decanted and then extracted with 3×25 ml ether. The organic (ether and benzene) phases are combined, washed with 2×50 ml water, and then dried and evaporated to dryness, to give 2.6 g N-(ethoxycarbonyl-methyl)-L.Phe.-L.Leu OCH$_3$ as a pale yellow oil. Rf=0.77 (CHCl$_3$/MeOH/H$_3$O 9/1/Sat.).

EXAMPLE 2

N-(carboxy-methyl)L.phenylalanine-L.leucine

N-(ethoxycarbonyl-methyl)-L.Phe.L.Leu methyl ester (25. g) is dissolved in a mixture of methanol (20 ml) and water (10 ml). NaOH 1N (13 ml) is added at 0° C. and the mixture is stirred for 1 hour at 0° C., and then 2 hours at 25° C. The methanol is evaporated off, and HCl 1N is added dropwise, at 0° C., to pH 2. The resulting precipitate is filtered and recrystallized from ether/MeOH 50:50, to give 1.35 g N(carboxymethyl)-L.Phe-L.Leu M.p.=196°-200° C. Rf (BuOH/AcOH/H$_2$O 4:1:1)=0.6.

EXAMPLE 3

N-(Carboxymethyl)L.phenylalanine-N(CH$_3$)L.Leucine

The procedure of Example 1 is used, except that L.Leucine methyl ester is substituted with N(CH$_3$)L.Leucine methyl ester, and that the resulting material is then treated as described in Example 2, to give, successively: N-(ethoxycarbonyl-methyl)-L.Phe-N(CH$_3$)L.Leu methyl ester, followed by N-(carboxy-methyl)-L.Phe-N(CH$_3$)L.Leu.

In this synthesis, the starting material, L.Phe-N(CH$_3$)-L.Leu OCH$_3$ TFA is obtained by condensing Boc Phe with N(CH$_3$)-L.Leu methyl ester in the presence of DDC and HOBT, followed by deprotection with TFA.

EXAMPLE 4

N-(carboxy-methyl)-L.phenylalanine-D.leucine

The compound is obtained as described in Example 1, substituting D.leucine for the L form in the starting material.

There are successively obtained N-(ethoxycarbonyl-methyl)-L.Phe-D.Leu methyl ester followed by (carboxymethyl)-L.Phe-D.Leu. M.P.=240° C.

EXAMPLE 5

N-(carboxy-methyl)-D.phenylalanine-L.leucine

The compound is obtained as described in Example 1, substituting D.phenylalanine for the L form in the starting material, to give, successively: N-(ethoxycarbonyl-methyl)-D.Phe-L.Leu methyl ester, and then N-(carboxy-methyl)-D.Phe-L.Leu. M.P.=234° C.

EXAMPLE 6

N-(carboxy-methyl)-D.phenylalanine-D.leucine

Obtained as described in Example 1, substituting L.leucine and L.phenylalanine with their D.isomers, to give, successively: N-(ethoxycarbonyl-methyl)-D.Phe-D.Leu methyl ester, and then N-[(carboxy)methyl]-D.Phe-D.Leu. M.P.=227° C.

EXAMPLE 7

N-(2-Ethoxycarbonyl-ethyl)L.Phe-L.Leu methyl ester 8.80 g Phe-Leu OCH$_3$ (obtained as the base from Phe-Leu OCH$_3$ TFA by action of triethylamine) are dissolved in 200 ml anhydrous benzene under a nitrogen atmosphere. Ethyl bromopropionate (5.8 ml) and K$_2$CO$_3$ (2.07 g) are added dropwise at 0° C. The mixture is heated at 80° C. for 4 hours. After cooling, the benzene phase is rapidly separated. 20 ml H$_2$O are then added, followed by the dropwise addition of 1N HCl to pH 2.

The benzene phase is separated; the acidic aqueous phase is washed with 3×50 ml ethyl acetate. The combined organic phases are dried and then evaporated to dryness, to give 2.94 g of a straw-yellow oil which is purified by column chromatography over silica gel with Et$_2$O/MeOH 9:1 as eluent, which gives 1.10 g N-(2-ethoxycarbonyl-ethyl)-L.Phe-L-Leu methyl ester as a colorless oil. Rf=0.81 (CHCl$_3$/MeOH/H$_2$O 0:1:Sat.).

EXAMPLE 8

N-(2-carboxy-ethyl)L.Phe-L.Leu 720 mg N-(2-ethoxycarbonyl-ethyl)-L.Phe-L.leu methyl ester are added to 10 ml MeOH. 7.3 ml 1N NaOH are added at 0° C. The mixture is stirred for 12 hours at room temperature. The mixture is made acidic to pH 3 with HCl and the aqueous phase is extracted with 3×20 ml ethyl acetate. The dried and evaporated organic phases give 510 mg N-(2-carboxy-ethyl)-L.Phe-L.Leu as a white solid. M.P.=161° C. Rf=0.51 (BuOH-/AcOH/H$_2$O).

EXAMPLE 9

N-(ethoxycarbonyl-methyl)-L.Phe-L.Ala methyl ester

This compound is obtained as in Example 1, substituting L.Phe-L.Leu OCH$_3$ TFA with L.Phe-L.Ala OCH$_3$ TFA, to give 1.10 g N-(ethoxycarbonyl-methyl)-L.Phe-L.Ala methyl ester as an oil. Rf=0.71 (CHCl$_3$/MeOH/-H$_2$O 9:1:Sat.

EXAMPLE 10

N-(carboxy-methyl)-L.Phe-L.Ala

The reaction is effected as in Example 2, using N-(ethoxycarbonyl-methyl)-L.Phe-L.Ala methyl ester (1 g) to give, after saponification and acidification, 88 mg N-(carboxy-methyl)-L.Phe-L.Ala. Rf=0.37 (BuOH/-MeOH/H$_2$O 4:1:1).

EXAMPLE 11

N-(2-mercapto-ethyl)-L.Phe t.butyl ester

In a tube, 0.9 ml freshly distilled thiiran C$_2$H$_4$S is added to 8.7 g oily L.Phe-OtBu obtained as the base from its hydrochloride. The tube is sealed and then heated at 100° C. for 5 hours. After cooling, the tube is opened and the sirupy liquid is distilled, to give 3.62 g N-(2-mercapto-ethyl)-L.Phe t.butyl ester. B.p.$_{0.5}$=130°–134° C.

EXAMPLE 12

N-(2-benzoylthio-ethyl)-L.Phe t.butyl ester 3.62 g N-(2-mercapto-ethyl)-L.Phe t.butyl ester are dissolved in 15 ml H$_2$O to which 628 mg K$_2$CO$_3$ are added. 1.51 ml Benzoyl bromide dissolved in 15 ml ether are slowly added. The mixture is stirred at room temperature for one hour. The resulting solid is suction filtered, washed with cold ether, and then with acidic water (pH 3–4), to give 1.6 g N-(2-benzoylthio-ethyl)L.-Phe t.butyl ester. M.P.=170°–172° C.

EXAMPLE 13

N-(2-benzoylthio-ethyl)-L.Phe 850 mg N-(2-benzoylthio-ethyl)-L.Phe t.butyl ester are mixed with 3.31 ml TFA in an ice-bath, and the mixture is stirred at room temperature for 12 hours. The white precipitate is filtered off and washed with ether to pH 5, to give 620 mg (N-2-benzoylthio-ethyl)L.Phe. M.P.=260° C.

EXAMPLE 14

N-(2-benzoylthio-ethyl)-L.Phe-L.Leu methyl ester 0.40 ml Triethylamine are added to a solution of 620 mg N-(2-benzoylthio-ethyl)-L.Phe (prepared as described in Example 13) and 254 mg L.Leu OCH$_3$ hydrochloride in a mixture of 40 ml CHCl$_3$ and 10 ml THF. After 5 minutes, 214 mg HOBT and 288 mg DCC are added.

After stirring for 48 hours, the DCU is filtered off and treated, to give 250 mg N-(2-benzoylthio-ethyl)L.Phe-L.Leu methyl ester. Rf=0.42 (CHCL$_3$/Et$_2$O 8:2).

EXAMPLE 15

N-(2-mercapto-ethyl)-L.Phe-L.Leu

Method A 250 mg N-(2-benzoylthio-ethyl)-L.Phe-L.Leu methyl ester are dissolved in 15 ml MeOH. 1.1 ml 1N NaOH is added thereto, and the mixture is stirred overnight at 25° C. under a nitrogen atmosphere. The methanol is evaporated off, 10 ml H$_2$O are added and the material is made acidic to pH 2–3, to give 65 mg N-(2-mercaptoethyl)-L.Phe-L.Leu as white crystals. Rf=0.9 (BuOH-/AcOH/H$_2$O 4:1:1).

Method B 5 g L.Phe-L.Leu methyl ester, as the base, are dissolved in 50 ml anhydrous benzene in a glass ampoule. 5 ml of freshly prepared thiiran, C$_2$H$_4$S, are added and the ampoule is sealed, and then heated in an oven at 80° C. for 2 hours. After cooling and opening the ampoule, a gelatinous precipitate is removed from the solution by filtration, and the filtrate is concentrated in vacuo, to give a yellow oil which, on column chromatography over alumina, gives 2.2 g N-(2-mercapto-ethyl)-L.Phe- L.Leu methyl ester. The latter is saponified under a nitrogen atmosphere in a solution of MeOH and 1N NaOH. After acidification and extraction with ethyl acetate, there are obtained 1.19 g N-(2-mercapto-ethyl)-L-Phe-L.Leu identical with the compound obtained according to Method A.

EXAMPLE 16

N-(2-Mercapto-ethyl)-L.Phe-L.Ala

Obtained as in Example 15 (Method B), by substituting L.Leu with L.Ala in the starting methyl ester, to give, from 3 g methyl ester, 720 mg N-(2-mercapto-ethyl)-L.Phe-L.Ala methyl ester. M.P.=61° C. Rf=0.80 (BuOH/MeOH/H$_2$O 4:1:1).

EXAMPLE 17

N-[(R,S)-3-Acetylthio-2-benzyl-propionyl]-L-leucine methyl ester

To a solution of 1.4 g 3-acetylthio-2-benzyl-propionic acid obtained by addition of thioacetic acid on benzylacrylic acid (obtained according to C. Mannich & K. Ritsert, 1924, Ber. 57, 1116) in 20 ml anhydrous THF, cooled to 0° C., are successively added a solution of 1.09 g L-leucine methyl ester hydrochloride and 0.84 ml triethylamine in 20 ml dry chloroform, and then a solution of 920 mg HOBT in 20 ml THF and, finally, a solution of 1.22 g DCC in 20 ml CHCl$_3$. The mixture is stirred at 0° C. for 4 hours, and then at 20° C. for 5 hours.

After filtration of the DCU formed, the material is evaporated to dryness, the residue is taken up into 40 ml ethyl acetate. It is then washed with 2×20 ml water, 1×20 saturated NaCl solution, 2×20 ml 10% citric acid solution, 3×20 ml saturated NaHCO$_3$ solution, 2×20 ml water, 1×20 ml saturated NaCl solution, and dried over Na$_2$SO$_4$.

The material is then evaporated to dryness, to give 1.9 g of a dark yellow oil. Yield: 87%. Rf=0.86 (CHCl$_3$/MeOH/H$_2$O; 9:1:Sat/). HPLC-Vr=28.3 ml in a sulfate 10$^{-2}$M(pH 4.4)/CH$_3$CN buffer 55:45.

EXAMPLE 18

N[(R,S)3-mercapto-2-benzyl-propionyl]-L.leucine 1.5 g of the compound of Example 17 are dissolved in 20 ml degassed methanol. 8.5 ml of a 1N sodium hydroxide solution are added at 0° C., under a nitrogen stream. The mixture is stirred 1 hour at 0° C. The methanol is evaporated off in vacuo; the resulting material is taken up into 20 ml degassed water and extracted with chloroform.

The aqueous phase is then made acidic to pH 1 with a 2N HCl solution. The resulting white precipitate dissolves on addition of 20 ml methanol. Powdered Zn (500 mg) is then added and the mixture is stirred at 20° C. for one hour.

The zinc is filtered and washed with 2×5 ml degassed MeOH. The methanol-water phases are combined and the methanol is evaporated in vacuo. The remaining aqueous phase is extracted with chloroform.

The material is evaporated to dryness, to give 1 g N(R,S-3-mercapto-2-benzyl-propionyl)-L.leucine as a white solid product, M.P.=50° C. Yield: 79%. HPLC, Vr=10.56 ml in acetate 10$^{-2}$M(pH 4.3)/CH$_3$CN buffer 60:40.

Elementary analysis for C$_{16}$H$_{23}$NO$_3$S: Calculated %: C, 62.1; H, 7.49; N, 4.53; S, 10.36 found %: 61.98 7.53 4.46 10.51.

NMR (DMSOd$_6$). Separate signals are noted for both diastereoisomers. HS=2.03 and 2.15 ppm (disappear on addition of D$_2$O). (HS)CH$_2$=2 multiplets centered at 2.37 and 2.56 ppm. CH—CH$_2$ ($\phi$)=complex broad signal centered at 2.61 ppm. H$_\alpha$(Leu)=4.06 and 4.17 ppm. CH$_{2\beta}$Leu=1.30 and 1.44 ppm. CH$\gamma$Leu=1.13 and 1.58 ppm. CH$_3$=0.65 and 0.80 ppm NH=8.07 and 8.18 ppm. aromatic H=7.13 ppm

EXAMPLE 19

N-[(RS)-3-acetylthio-2-benzyl-propionyl]glycine methyl ester

To a solution of 2.34 g 3-acetylthio-2-benzylpropionic acid in 20 ml THF cooled to 0° C. are successively added a solution of 1.23 g glycine methyl ester hydrochloride and 1.37 ml triethylamine in 20 ml chloroform, a solution of 1.50 g HOBT in 15 ml THF, and a solution of 2.22 g DCC in 10 ml CHCl$_3$. The mixture is stirred at 0° C. for one hour, and then at 20° C. for 5 hours. After filtration of the DCU formed, the material is treated as described for the compound of Example 17, to give 2.6 g N-[(R,S)-3-thioacetyl-2-benzyl-propionyl]-glycine methyl ester as a pale yellow oil. Yield: 87%. Rf=0.76 in CHCl$_3$/MeOH/H$_2$O 9:1:Sat. HPLC, Vr=9.12 ml in acetate 10$^{-2}$M(pH 4.3)/CH$_3$CN 55:45 buffer.

EXAMPLE 20

N-[(R,S)-3-mercapto-2-benzyl-propionyl]glycine 960 mg of the compound of Example 19 are dissolved in 20 ml degassed MeOH. 6.6 ml of a 1N sodium hydroxide solution are added at 0° C. under a nitrogen atmosphere, and the mixture is stirred at 0° C. for one hour. The methanol is evaporated in vacuo; after which the residue is taken up into 15 ml water and extracted with 2×5 ml CHCl$_3$.

The aqueous phase is made acidic with a 2N HCl solution to pH 1. 20 ml degassed MeOH are added, followed by 300 mg powdered Zn, and the material is then stirred at 20° C. for one hour.

The zinc is filtered off and washed with 2×5 ml MeOH. The methanol-water phases are combined and the methanol is evaporated in vacuo. The aqueous phase is then extracted with 3×10 ml CHCl$_3$, and evaporated to dryness, to give 500 mg (R,S-3-mercapto-2-benzyl-propionyl)glycine as a white solid. M.P.=138° C. Yield: 64%. HPLC, Vr=6.48 ml in acetate 10$^{-2}$M(pH 4.3)/CH$_3$CN 70:30 buffer.

Analysis: for C$_{12}$H$_{15}$NO$_3$S: calculated %: C, 56.9; H, 5.97; N, 5.53; S, 12.66 found %: 56.6 6.01 5.62 12.48.

NMR (DMSOd$_6$) a single series of signals for both enantiomers. HS=2.20 ppm (disappears on addition of D$_2$O). (HS)CH$_2$=2.34 and 2.57 ppm. CH—CH$_2$ multiplet centered at 2.64 ppm. CH$_2$(Gly)=3.66 ppm. aromatic H's=7.17 ppm. NH=8.28 ppm.

EXAMPLE 21

N-[(R,S)-3-acetylthio-2-benzyl-propionyl]-L.alanine methyl ester

To a solution cooled to 0° C. of 1.600 g 3-acetylthio-2-benzyl-propionic acid in 20 ml anhydrous THF are successively added a solution of 940 mg L.alanine methyl ester hydrochloride and 1 ml triethylamine in 20 ml CHCl₃, a solution of 1.03 g HOBT in 10 ml THF, and a solution of 1.4 g DCC in 10 ml CHCl₃. The mixture is stirred for 1 hour at 0° C. and then for 5 hours at 20° C. It is then treated as in the foregoing Examples, to give 1.75 g N-[(R,S)3-acetylthio-2-benzyl-propionyl]-L.alanine methyl ester as a yellow oil. Yield: 80%. Rf=0.77 in CHCl₃/MeOH/water 9:1:Sat. HPLC, Vr=10.32 in acetate $10^{-2}$M(pH 4.3)/CH₃CN 55:45 buffer.

EXAMPLE 22

N-[(R,S)-3-Mercapto-2-benzyl-propionyl]-L.alanine 1.54 g of the compound of Example 21 are dissolved in 20 ml degassed methanol, and 10 ml of 1N sodium hydroxide solution are added thereto at 0° C. and under a nitrogen atmosphere. The mixture is stirred at 0° C. for 2 hrs. The methanol is evaporated in vacuo and the resulting material is taken up into 20 ml water. The alkaline aqueous phsase is extracted with 2×5 ml chloroform. The aqueous phase is made acidic with 2N HCl to pH 1, after which 20 ml degassed MeOH and 300 mg powdered Zn are added. The mixture is stirred at 20° C. for 1 hour. The zinc powder is filtered off and washed twice with methanol. The aqueous and methanol phases are combined. The methanol is evaporated in vacuo and the remaining aqueous phase is extracted with chloroform, and then evaporated to dryness, to give 1.07 g N-[(R,S)-3-mercapto-2-benzyl-propionyl]-L.alanine as a white solid. M.P.<50° C. Yield: 84%. HPLC, Vr=5.4 ml in acetate $10^{-2}$M(pH 4.3)/CH₃CN 65:35 buffer.

Analysis for C₁₃H₁₇NO₃S: calculated %: C, 58.40; H, 6.41; N, 5.24; S, 11.99 found %: 58.23 6.60 5.31 11.64.

NMR (DMSOd₆) one set of signals is noted for each diastereoisomer. HS=2.06 and 2.12 ppm (disappear on addition of D₂O). (HS)CH₂ multiplets centered at 2.34 and 2.58 ppm. (HS)CH₂(φ) complex broad signal centered at 2.75 ppm NH=8.17 and 8.27 ppm. H₂Ala=4.08 and 4.15 ppm. CH₃Ala=1.05 and 1.20 ppm. aromatic H's=7.17 ppm

EXAMPLE 23

O-Benzyl-N-[(R,S)-3-benzoylthio-2-benzylpropionyl]-L.serine methyl ester

To a solution, cooled to 0° C., of 500 mg 3-benzoylthio-2-benzyl-propionic acid in 10 ml THF(anhydrous) are successively added a solution of 408 mg O-benzyl-L.serine methyl ester hydrochloride and 0.24 ml triethylamine in 6 ml CHCl₃, a solution of 250 mg HOBT in 5 ml anhydrous THF and, finally, a solution of 376 mg DCC in 5 ml CHCl₃. The mixture is stirred for 1 hour at 0° C. and for 5 hours at 20° C. After filtration of the DCU formed, the material is treated as in the foregoing Examples, to give 720 mg O-benzyl-N-[(R,S)-3-benzoylthio-2-benzyl-propionyl]-L.serine methyl ester as a white solid. Yield: 88%. M.P.=62°-64° C. Rf=0.84 in CHCl₃/MeOH/water 9:1:Sat. HPLC, Vr=9.84 ml in acetate $10^{-2}$M(pH 4,3)/CH₃CN 30:70 buffer.

EXAMPLE 24

O-Benzyl-N-[(R,S)-3-mercapto-2-benzyl-propionyl]L.serine 660 mg of the compound of Example 23 are dissolved in 10 ml degassed MeOH. 3 ml of a 1N sodium hydroxide solution are added at 0° C. under a nitrogen atmosphere. The mixture is stirred for 1 hour at 0° C. The methanol is evaporated in vacuo, and the material is taken up into 10 ml water and extracted twice with chloroform. The aqueous phase is made acidic to pH 1 with 2N HCl. 10 ml methanol and 150 mg powdered Zn are added thereto, and the mixture is stirred for 1 hour at 20° C. The Zn is filtered, washed with 2×5 ml MeOH. The aqueous and methanol phases are combined, and the methanol is evaporated in vacuo. The aqueous phase is extracted with chloroform. After evaporation, O-benzyl-N-[(R,S)-3-mercapto-2-benzyl-propionyl]-L.serine (350 mg) is obtained as a very pale yellow oil. Yield: 70%. HPLC, Vr=6.96 ml in acetate $10^{-2}$M(pH 4.3)/CH₃CN 55:45 buffer.

NMR (DMSOd₆): HS=2.02 and 2.12 ppm (disappear on addition of D₂O). (HS)CH₂=2.33 and 2.56 ppm. CHCH₂(φ)=broad signals centered at 2.70 ppm. Hα-Ser=4.37 and 4.44 ppm. CH₂βSer=3.46 and 3.62 ppm. OCH₂=4.32 and 4.42 ppm. aromatic H's=7.17 ppm. NH=8.25 and 8.33 ppm.

Analysis for C₂₀H₂₃NO₄S: calculated %: C, 64.34; H, 6.21; N, 3.75; S, 8.58 found % 64.30 6.31. 3.87 8.66

EXAMPLE 25

N-[(R,S)-3-acetylthio-2-p-fluorobenzylpropionyl]-L.leucine methyl ester

To a solution of 1.54 g 3-acetylthio-2-p.fluorobenzyl-propionic acid in 20 ml anhydrous THF cooled to 0° C. are successively added a solution of 1.15 g L.leucine methyl ester hydrochloride and 0.85 ml triethylamine in 20 ml dry chloroform, a solution of 930 mg HOBT in 20 ml THF and, finally, a solution of 1.24 g DCC in 20 ml CHCl₃. The mixture is stirred for one hour at 0° C., and then for 5 hours at 20° C. 1.95 g dark yellow oil are obtained after filtration and treatment as in Example 17. Yield: 88%. Rf=0.87 (CHCl₃/MeOH/H₂O 0.1:Sat.). HPLC, Vr=30 ml in acetate $10^{-2}$M(pH 4.3)/CH₃CN 55:45 buffer.

EXAMPLE 26

N-[(R,S)-2-mercapto-3-p.fluorobenzylpropionyl]-L.leucine 1.8 g of the compound of Example 25 are dissolved in 20 ml degassed methanol. 9.8 ml of a 1N sodium hydroxide are added thereto at 0° C. and under a nitrogen stream. The methanol is evaporated in vacuo and the residue is taken up into 20 ml degassed water and extracted with chloroform. The aqueous phase is then made acidic to pH 1 with a 2N HCl solution. The resulting white precipitate dissolves on addition of 20 ml methanol. 500 mg powdered Zn are added thereto, and the mixture is stirred for 1 hour at 20° C. The zinc is filtered and washed with 2×5 ml degassed MeOH. The methanol and aqueous phases are combined and the methanol is evaporated in vacuo.

The aqueous phase is then extracted with 3×10 ml CHCl₃, and evaporated to dryness, to give 1.08 g of the title compound as a white solid. Yield: 68%. M.p. <50° C. HPLC, Vr=11 ml in acetate $10^{-2}$M(pH 4.3)/CH₃CN 60:40 buffer.

NMR (DMSOd₆): HS=2.04 and 2.12 ppm (disappear on addition of D₂O). (HS)CH₂=2 multiplets centered at 2.40 and 2.58 ppm. CHCH₂(φ)=complex broad signal centered at 2.63 ppm. HαLeu=4.06 and 4.17 ppm. CH₂βLeu=1.31 and 1.44 ppm. CHγLeu=1.13 and 1.58 ppm. CH₃=0.65 and 0.81 ppm. NH=8.08 and 8.19 ppm. aromatic H's=2 broad signals centered at 7.28 and 7.95 ppm.

Analysis for $C_{16}H_{22}O_3NFS$: calculated %: C, 58.70; H, 6.78; N, 4.28; S, 9.78, found % 58.55 6.60 4.32 9.98.

EXAMPLE 27

N-[(S)-2-benzoylthio-3-phenyl-propionyl]-L.leucine

To a solution of 11.2 g R,2-bromo-3-phenyl-propionic acid in 30 ml THF are added 8.9 g L-leucine methyl ester hydrochloride dissolved in a mixture of 100 ml $CHCl_3$ and 6.86 ml $NEt_3$. To the resulting solution are added 7.5 g HOBT and 10.1 g DCC. After stirring for 1 hour at 0° C., and then for 12 hours at 25° C., the DCU formed is filtered off and the material is treated according to the usual procedure, to give, on evaporation of the ethyl acetate, 12.5 g N-[(R)-2-bromo-3-phenylpropionyl]-L.leucine methyl ester as white crystals. M.P.=121° C.

At 0° C., 30 ml 1N NaOH are added to a solution of 10.5 g of the preceding compound in 100 ml MeOH. The mixture is stirred for 1 hour at 0° C. and then 4 hours at 25° C., and is then made acidic with HCl. The resulting precipitate is collected and crystallized from ethyl acetate, to give 9.07 g N-[(R)-2-bromo-3-phenyl-propionyl]-L.leucine, M.P.=158° C.

1.76 g thiobenzoic acid dissolved in 40 ml water, in the presence of 2.17 g $K_2CO_3$, are added to a mixture of 7.1 g N-[(R)-2-bromo-3-phenyl-propionyl]-L.leucine in 30 ml water and 1.74 g Na bicarbonate; The mixture is stirred for 12 hours at 25° C. Acidification with HCl 6N gives a pale yellow oil which is extracted with ethyl acetate. The material is washed with water. The organic phase is dried and evaporated to dryness, to give 7.9 g N-[(S)-2-benzoylthio-3-phenyl-propionyl]-L.leucine as an oil which crystallizes slowly. M.P.=74°–78° C. Rf=0.80 in $BuOH/MeOH/H_2O$ 4:1:1.

EXAMPLE 28

N-[(S)-2-mercapto-3-phenyl-propionyl]-L.leucine 2 g N-[(S)-2-benzoylthio-3-phenyl-propionyl]-L-leucine dissolved in 10 ml MeOH are stirred at 0° C. for 1 hour with 10 ml 1N NaOH, and then for 4 hours at 25° C. under a nitrogen atmosphere. The methanol is evaporated off, the material is taken up into water and made acidic to pH 1 with 1N HCl. The resulting gummy precipitate is extracted with ethyl acetate. The organic phase is dried, and evaporated in vacuo, to give 1.45 g N-[(S)-2-mercapto-3-phenyl-propionyl]-L-leucine which crystallizes slowly. M.P.=67°–71° C.

EXAMPLE 29

N-[(S)-2-acetylthio-3-phenyl-propionyl]-L.leucine methyl ester 3 g S,2-acetylthio-3-phenyl-propionic acid (obtained by action of thioacetic acid on R,2-bromo-3-phenyl-propionic acid) dissolved in 30 ml $CHCl_3$ are added to a solution of 2.5 g L-leucine methyl ester hydrochloride. 5 ml $NEt_3$ are added thereto, followed by 2 g HOBT and 2.8 g DCC. After stirring for 1 hour at 0° C., and for 12 hours at 25° C., the resulting DCU is filtered and the material is treated according to the usual procedure, to give 4.1 g N-[(S)-2-acetylthio-3-phenyl-propionyl]-L-leucine methyl ester as an oil. Rf=0.85 in $CHCl_3/MeOH/H_2O$ 9:1:Sat.

EXAMPLE 30

N-[(S)-2-mercapto-3-phenyl-propionyl]-L.leucine methyl ester 2 g of the compound of Example 29 are stirred for 12 hours in a saturated HCl methanol solution, under a nitrogen atmosphere. The mixture is evaporated to dryness, taken up into water and extracted with ether. The organic phase is dried and evaporated to dryness, to give 750 mg N-[(S)-2-mercapto-3-phenyl-propionyl]-L-leucine methyl ester as an oil. Rf=0.70 in $CHCl_3/Et_2O$ 5:5.

EXAMPLE 31

N-[(S)-2-acetylthio-3-phenyl-propionyl]-L.leucine

This compound is obtained as in Example 27, except that the thiobenzoic acid is substituted with thioacetic acid, to give a pale yellow oil which crystallizes slowly. M.P.=50° C. Yield: 84%. Rf=0.80 in $BuOH/MeOH/H_2O$ 4:1:1.

EXAMPLE 32

N-[(S)-2-mercapto-3-phenyl-propionyl]-L.alanine

Obtained according to the methods successively used in Examples 27 and 28, substituting L-leucine methyl ester with L-alanine methyl ester. This procedure gives N-[(S)-2-mercapto-3-phenyl-propionyl]-L-Ala as white crystals. M.P.=42° C.

EXAMPLE 33

N-[(S)-2-acetylthiomethylthio-3-phenyl-propionyl]-L.leucine 0.42 ml acetylthiochloromethane dissolved in MeOH are added to a mixture of 1.1 g N-[(S)-2-mercapto-3-phenyl-propionyl]-L.leucine (obtained as in Example 28) and 552 mg $K_2CO_3$ in water. The mixture is stirred for 20 hours at room temperature, evaporated to dryness, and taken up into ethyl acetate, after which it is dried and evaporated, to give 252 mg N-[(S)-2-acetyl-thiomethylthio-3-phenyl-propionyl]-L.leucine as an oil, after purification by column chromatography over alumina in $CHCl_3/MeOH$ 7:3. Rf=0.77 ($CHCl_3/MeOH$ 5:3).

EXAMPLE 34

N-[(S)-2-benzoylthio-ethylthio-3-phenyl-propionyl]-L.leucine 1.33 g N-[(S)-2-mercapto-3-phenyl-propionyl]-L.leucine (obtained as in Example 28) are dissolved in 30 ml water in the presence of 685 mg $K_2CO_3$. 1.32 g 1-benzoylthio-2-bromoethane (obtained by direct action of benzoyl bromide on thiiran according to B. HANSEN, Acta Chem. Scand. 11, 537 (1957)) dissolved in 10 ml MeOH are added at 0° C. The mixture is stirred for 48 hours at 25° C. A slight downy precipitate is filtered off and the material is made acidic to pH 2 with 6N HCl. It is extracted with 3×20 ml ethyl acetate, dried and evaporated to dryness, to give 1.50 g of the desired compound as an oil which crystallizes slowly. M.P.=62°–68° C.

EXAMPLE 35

N-[(S)-2-mercapto-ethylthio-3-phenyl-propionyl]-L.leucine 800 mg of the compound of Example 34 are dissolved in 10 NaOH and 3.4 ml 1N NaOH are added thereto over 30 minutes, under a nitrogen atmosphere. The material is left standing for 4 hours at 25° C., under a nitrogen atmosphere, 20 ml H$_2$O are added thereto, MeOH is evaporated off, after which the material is filtered and made acidic to pH 1 with 1N HCl. It is extracted with 3×20 ml ether, dried and evaporated to dryness, to give 544 mg of a colorless oil. Rf=0.92 in BuOH/AcOH/H$_2$O 4:1:1, corresponding to N-[(S)-2-mercapto-ethylthio-3-phenyl-propionyl]-L.leucine.

EXAMPLE 36

N-[(S)-2-mercapto-ethylthio-3-phenyl-propionyl]-L.alanine

Using the procedure of Example 34, except that N-[(S)-2-mercapto-3-phenyl-propionyl]-L.leucine is substituted with N-[(S)-2-mercapto-3-phenyl-propionyl]-L-alanine (obtained as in Example 32), there is obtained N-[(S-2-benzoylthio-ethylthio-3-phenyl-propionyl]L-alanine. This derivative, on treatment as described in Example 35, gives N-[(S)-2-mercaptoethylthio-3-phenyl-propionyl]-L.alanine, as a thick oil which crystallizes slowly. M.P.=34° C.

EXAMPLE 37

Preparation of N-Boc, N'-(2-ethoxycarbonyl-propionyl)-1,1-diamino-2-phenyl-ethane (a) N-t.butoxycarbonyl, N-benzyloxycarbonyl-1,1-diamino-2-phenyl-ethane 1.5 g Boc L-Phe-azide are heated to 80° C. for 1 hour in 10 ml anhydrous toluene. An isocyanate forms, which is not isolated. After cooling the solution, 0.55 ml benzyl alcohol are added thereto, and the material is again heated at 80° C. for one hour. After cooling, 0.9 g N-Boc, N'-Z-1,1-diamino-2-phenyl-ethane crystallizes out of the solution, M.p.=165° C.

(b) N-Boc 1,1-diamino-2-phenyl-ethane 0.4 g N-Boc, N'-Z-1,1-diamino-2-phenyl-ethane are dissolved in 10 ml methanol in the presence of 25 g Pd/C. Hydrogenation under ordinary pressure gives, after filtration and evaporation to dryness, 0.3 g N-Boc 1,1-diamino-2-phenyl-ethane as a pale yellow solid. M.p.=40°–50° C.

(c) Title compound 270 mg methyl malonic (R,S) acid monomethyl ester dissolved in 10 ml THF are added to a solution of 436 mg N-Boc, 1,1-diamino-2-phenyl-ethane, 283 mg HOBT and 381 mg DCC in 10 ml CHCl$_3$. After 4 hours at room temperature, the DCU formed is filtered off and the solution is treated under the usual peptidic coupling conditions to give 544 mg of a pale yellow solid. Rf=0.80 in CHCl$_3$/MeOH/H$_2$O 9:1:Sat, N-Boc,N'-(2-ethoxycarbonylpropionyl)-1,1-diamino-2-phenyl-ethane (SR+SS).

EXAMPLE 38

N-Boc, N'-(2-carboxy-propionyl)-1,1-diamino-2-phenyl-ethane 200 mg of the compound obtained in Example 37 are dissolved in 10 ml MeOH. 1.5 ml 1N NaOH are added thereto. The mixture is stirred for 4 hours at room temperature; MeOH is evaporated off; the material is taken up into H$_2$O and made acidic to pH 2. It is then extracted with ethyl acetate, dried and evaporated to dryness, to give 130 mg N-Boc, N'(2-carboxy-propionyl)-1,1-diamino-2-phenyl-ethane (SR+SS) as white crystals, M.P.=170°–171° C.

EXAMPLE 39

N-(2-carboxy-propionyl)-1,1-diamino-2-phenyl ethane 100 mg of the compound obtained in Example 38 are stirred with 0.4 ml TFA for 1 hour at 25° C. On evaporation to dryness and after taking up into ethyl ether, there are obtained 60 mg N-(2-carboxy-propionyl)-1,1-diamino-2-phenyl ethane (RR+SS). Rf=0.35 in BuOH/AcOH/H$_2$O 4:1:1.

EXAMPLE 40

N-carboxymethyl, N'-(2-carboxy-propionyl)-1,1-diamino-2-phenyl-ethane 300 mg of the compound obtained in Example 37 are stirred for 1 hour at 0° C. with 1 ml TFA. After evaporation to dryness and addition of ether, the resulting white solid is dried in vacuo, suspended in anhydrous benzene, and refluxed for 12 hours with 0.1 ml ethyl bromoacetate.

After filtration, N-ethoxycarbonylmethyl, N'-(2-ethoxycarbonyl-propionyl)-1,1-diamino-2-phenyl-ethane is collected as a pale yellow oil which is saponified without purification to give 52 mg N-carboxymethyl, N'(2-carboxy-propionyl)-1,1-diamino-2-phenyl-ethane (RR+SS). Rf=0.42 in BuOH/AcOH/H$_2$O 4:1:1.

EXAMPLE 41

N-(2-mercapto-ethyl), N'(2-carboxy-propionyl)-1,1-diamino-2-phenyl-ethane (RR+SS)

Obtained by direct action of thiiran in a sealed tube on 50 mg of the compound of Example 39 according to the method described in Example 25 (Method B). M.P.=180°–190° C.

EXAMPLE 42

Boc 2-amino-3-phenyl-1-carboxymethylthio-propane 2.3 g of Boc-L-phenylalaninol p.toluenesulfonic ester (obtained by reduction of t-Boc-L-Phe to the alcohol, followed by action of tosyl chloride) dissolved in 50 ml MeOH are added to an aqueous solution of thioglycolic acid disodium salt. After refluxing for 12 hours, the reaction mixture is filtered, the solution is made acidic and extracted with ethyl acetate, to give 700 mg of a thick oil which is submitted to a column chromatrography over alumina with a mixture Et$_2$O/MeOH 7:3.

There are obtained 550 mg Boc-2-amino-3-phenyl-1-carboxymethylthio-propane. M.P.=95° C. Rf=0.63 in CHCl$_3$/MeOH 7:3.

EXAMPLE 43

(2-Amino-3-phenyl-1-carboxymethylthio)-propane trifluoroacetate 400 mg of the compound described in Example 42 are stirred for 1 hour at 25° C. with 1 ml TFA. After evaporation to dryness, the material is taken up into ether, to give 300 mg (2-amino-3-phenyl-1-carboxymethylthio)-propane trifluoroacetate as a white powder. Rf=0.41 in BuOH/MeOH/H$_2$O 4:1:1.

EXAMPLE 44

2-Carboxymethylamino-3-phenyl-1-carboxymethylthio-propane 250 mg of the compound described in Example 43 are suspended in 10 ml anhydrous benzene. 0.15 ml triethyl amine and 0.21 ml ethyl bromoacetate are added thereto. The resulting solution is refluxed for 10 hours, after which it is filtered, dried and evaporated to dryness. The resulting oil is submitted to a column chromatography over silica gel in Et$_2$O/MeOH 8:2, to give 125 mg 2-carboxymethylamino-3-phenyl-1-carboxymethylthio-propane. Rf=0.57 in CHCl$_3$/MeOH 8:2.

EXAMPLE 45

2-(2-Mercapto-ethylamino)-3-phenyl-1-carboxymethylthio-propane 150 mg of the compound described in Example 43 are treated as in Example 15 (Method B) to give 42 mg 2-(2-mercapto-ethylamino)-3-phenyl-1-carboxymethylthio-propane. M.P.=201° C.

EXAMPLE 46

N-(Boc-2-amino-3-phenyl-1-propyl)-L-leucine methyl ester 2 g Boc-L.Phe-alaninol p.toluenesulfonic ester are added to a solution of 1.4 g L-leucine methyl ester (as the base) in 10 ml dioxan. The mixture is refluxed for 2 hours. The solution is evaporated to dryness and taken up into ether. The resulting precipitate is filtered and dried, to give 1.1 g N-(Boc-2-amino-3-phenyl-1-propyl)-L.Leucine methyl ester. M.P.=61° C.

EXAMPLE 47

N-(2-carboxymethylamino-3-phenyl-1-propyl)-L-leucine 500 mg of the compound described in Example 46 are stirred for 1 hour with 2 ml TFA, after which the mixture is evaporated to dryness, ether is added thereto, to give a white solid which is dried in vacuo. The product is suspended without further purification in 20 ml anhydrous benzene and 0.2 ml triethylamine and 0.15 ml ethyl bromoacetate are added thereto. The solution is then refluxed for 15 hours, after which it is filtered and evaporated to dryness. The resulting oil is purified by column chromatography over alumina, with Et$_2$O/MeOH 9:1, to give 120 mg N-(2-carboxymethylamino-3-phenyl-1-propyl)-L.Leucine methyl ester. M.P.=40°-50° C.

100 mg of the above product are dissolved in 20 ml methanol and NaOH is added thereto to pH 9. After stirring for 2 hours, the material is made acidic to pH 4 with HCl, extracted with ethyl acetate and evaporated to dryness, to give 23 mg N-(2-carboxymethylamino-3-phenyl-1-propyl)-L.leucine M.F. 147°-151° C.

EXAMPLE 48

N-[2-(2-mercapto-ethylamino)-3-phenyl-1-propyl]-L.leucine

Obtained as in Example 15 (Method B), substituting L-Phe-L-Leu methyl ester with 200 mg N-(2-amino-3-phenyl-1-propyl)-L-leucine methyl ester obtained from the compound of Example 46 by action of TFA.

Action of thiiran and saponification under nitrogen give 32 mg N-[2-(2-mercapto-ethylamino)-3-phenyl-1-propyl]-L-leucine. M.P. 48° C.

EXAMPLE 49

1-[Ethoxycarbonylmethyl]-L.prolylalanine methyl ester

To a suspension of 5 g (16 mmoles) of L-propyl-L-alanine methyl ester trifluoroacetate in anhydrous benzene is added 1.76 ml triethylamine in 2 g ethyl bromoacetate. The solution is refluxed for 18 hours. The reaction is treated by the procedure described in Example 1, to give 2.05 g (45%) of an oily product. Rf=0.73 (CHCl$_3$/MeOH/Water=9:1:Sat).

EXAMPLE 50

1[Carboxymethyl]-L-Propyl-L-Alanine

This compound is obtained by a procedure similar to that described in Example 2, from 2 g 1[ethoxymethyl]-L.prolyl-L-alanine methyl ester, to give 900 mg 1[carboxymethyl]-L-propyl-L-alanine (50%) M.P.=158° C. Rf=0.42 (BuOH/MeOH/H$_2$O 4:1:1).

EXAMPLE 51

N-[3-Phenylacetylthio-2-benzyl-propanol]-glycine benzyl ester (a) 3-Mercapto-2-benzylpropanoic acid To a solution of 3-acetylthio-2-benzyl-propanoic acid (2.7 g; 11 mmoles) in 20 ml degassed MeOH is added at 0° C. a degassed NaOH solution (1 g, 25 mmoles) in 20 ml degassed water. After 1 hour at 0° C., the mixture is stirred for 4 hours at room temperature. The solvents are evaporated off and the residue is dissolved in degassed water (20 ml) and extracted with 10 ml CHCl$_3$. To the aqueous layer are then added, at 0° C., 20 ml degassed MeOH, 13 ml 3N HCl and 1 g Zn powder, after which the mixture is stirred for 1.5 hours at the same temperature. After filtration, MeOH is evaporated off and the aqueous layer is extracted with 3×20 ml degassed chloroform. The chloroform layer is dried over Na$_2$SO$_4$ and evaporated, to give 1.9 g (85%) of a colorless oil. Rf=0.67 (CHCl$_3$/MeOH 7:3).

(b) 3-Phenylacetylthio-2-benzyl-propanoic acid

To an ice-cold solution of 600 mg (3 mmoles) 3-mercapto-2-benzyl-propanoic acid in 5 ml degassed water are added 6.4 ml 1N NaOH and 0.45 ml (3.4 mmoles) φCH$_2$CO Cl. After 15 minutes at 0° C., the mixture is stirred for 3 hours at room temperature. The solution is then acidified to pH 4 with 1N HCl and extracted with Et$_2$O (3×5 ml).

The ethereal layer is washed, dried over Na$_2$SO$_4$, and evaporated, to give 960 mg of a white solid (99%). Rf=0.77 (CHCl$_3$/MeOH 7:3).

(c) Title compound

The compound is obtained by a procedure similar to that described in Example 17.

From 560 mg (1.78 mmoles) 3-phenylacetylthio-2-benzylpropanoic acid and 600 mg (1.78 mmoles) glycine benzyl ester p.tosylate were obtained 660 mg (80%) of the title compound, as a white solid. M.P.=82±1° C. Rf=0.77 (CHCl$_3$/MeOH/water 9:1:Sat.). HPLC, V$_r$=7.4 ml in CH$_3$CN/NH$_4$AcO buffer (10$^{-2}$M, pH 4.2) 70:30.

EXAMPLE 52

N-[3-benzoylthio-2-benzyl-propanoyl]-glycine benzyl ester

The compound is obtained by a procedure similar to that described in Example 17.

From 475 mg (1.58 mmoles) 3-benzoylthio-2-benzyl-propanoic acid and 532 mg (1.58 mmoles) glycine benzyl ester p.tosylate were obtained 680 mg (90%) of the title compound as a white solid recrystallized from Et$_2$O. M.P.=80±1° C. Rf=0.85 (CHCl$_3$/MeOH/Water 9:1:Sat). HPLC, Vr=7.7 ml in CH$_3$CN/NH$_4$AcO buffer (10$^{-2}$M; pH 4.2) 70:30.

EXAMPLE 53

N-[3-Acetylthio-2-benzylpropanoyl]glycine benzyl ester

To a stirred ice-cold solution of 2.85 g (12 mmoles) 3-acetylthio-2-benzylpropanoic acid in 20 ml THF are successively added a mixture of 4.04 g (12 mmoles) glycine benzyl ester p.tosylate and 1.71 ml triethylamine in 20 ml CHCl$_3$, a solution of 1.83 g (12 mmoles) HOBT in 15 ml THF, and a solution of 2.63 g (12.8 mmoles) DCC in 10 ml CHCl$_3$.

After 1 hour, the mixture is allowed to come to room temperature and is then stirred overnight. The reaction mixture is then treated according to the procedure of Example 17, to give 3 g of a white solid recrystallized from Et$_2$O (75%). M.P. 89±1° C. Rf=0.80 (CHCl$_3$/MeOH/water 9:1:Sat.).

EXAMPLE 54

N-[3-Acetylthio-2-benzylpropanoyl]glycine(p.fluoro)-benzylester

This compound is obtained by a procedure similar to that described in Example 53.

From 1 g (4.2 mmoles) 3-acetylthio-2-benzyl-propanoic acid and 1.49 g (4.2 mmoles) glycine (p.fluoro)-benzylester p.tosylate are obtained 1.18 g (70%) of a white solid recrystallized from Et$_2$O. M.P.=72±1° C. Rf=0.75 (CHCl$_3$/MeOH/Water 9:1:Sat.).

EXAMPLE 55

N-[3-Acetylthio-2-benzylpropanoyl]-glycine-2,2,2-trifluoroethyl ester

The title compound is obtained by a procedure similar to that described in Example 53, from 1 g (4.2 mmoles) 3-acetylthio-2-benzylpropanoic acid and 1.14 g (4.2 mmoles) glycine-2,2,2-trifluoroethyl ester trifluoroacetate, to give 1.2 g (82%) of an oily product which cristallizes slowly. M.P.=56±1° C. Rf=0.77 (CHCl$_3$/MeOH/Water 9:1:Sat.).

EXAMPLE 56

N-[3-Acetylthio-2-benzylpropanoyl]glycine benzylamide

The title compound is obtained according to the procedure described in Example 53, from 1 g (4.2 mmoles) 3-acetylthio-2-benzylpropanoic acid and 1.17 g (4.2 mmoles) glycine benzylamide trifluoroacetate, to give 1.32 g (79%) of a white solid. M.P.=62° C. Rf=0.42 (CHCl$_3$/MeOH/Water 9:1:Sat.).

EXAMPLE 57

N-[3-Mercapto-2-benzyl-propanoyl]glycine benzyl ester (a) 1,1'-Dithiobis(2-benzyl-3-propanoic)acid To a solution of 13 g 3-acetylthio-2-benzylpropanoic acid in 70 ml MeOH is added at 0° C. a solution of 4.9 g NaOH in 50 ml H$_2$O. After 1 hour at 0° C., the mixture is stirred for 4 hours at room temperature. A solution of I$_2$ in ethanol (0.3M) is added dropwise until a persistent yellow color is obtained. The solvents are evaporated and the residue is dissolved in water. The aqueous layer is acidified to pH 2 with 3N HCl and extracted with Et$_2$O. The ethereal layer is washed, dried and evaporated, to give 10 g (95%) of an oily product which crystallizes slowly. Rf=0.81 (BuOH/AcOH/Water 4:1:1).

(b) Title compound

To a solution of 1 g (2.56 mmoles) 1,1'-dithiobis-(2-benzyl-3-propanoic)acid in THF are added, successively, a mixture of 1.73 g (5.12 mmoles) glycine benzyl ester p.tosylate and 0.72 ml triethylamine, a solution of 0.77 g (5.12 mmoles) HOBT in THF, and a solution of 1.1 g (5.12 mmoles) DCC in CHCl$_3$. The reaction mixture is treated according to the procedure of Example 17, to give 1.53 g (87%) 1,1'-dithiobis(2-benzyl-3-propanoyl)-bis-glycine benzyl ester. Rf=0.91 (CHCl$_3$/MeOH/H$_2$O 9:1:Sat.).

The title compound is obtained by stirring for 2 hours 1,1'-dithiobis(2-benzyl-3-propanoyl)bis-glycine benzyl ester in a mixture of MEOH and 3N HCl with 500 mg Zn powder.

After filtration and extraction with CHCl$_3$, an oily product is obtained in a yield of 76%. Rf=0.76 (CHCl$_3$/MeOH/H$_2$O 9:1:Sat.). HPLC, Vr=5 ml in CH$_3$CN/NH$_4$AcO buffer (10$^{-2}$M, pH 4.2).

EXAMPLE 58

N-[3-Mercapto-2-benzyl-propanoyl]glycine(p.fluoro)-benzyl ester

The title compound is obtained by a procedure similar to that described in Example 57, using glycine(p.-fluoro)benzyl ester p.tosylate instead of glycine benzyl ester p.tosylate.

Oily product. Yield 75%. Rf=0.74 (CHCl$_3$/MeOH/H$_2$O 9:1:Sat.).

EXAMPLE 59

N-[3-Mercapto-2-benzyl-propanoyl]glycine(2,2,2-trifluoro)ethyl ester

The title compound is obtained by a procedure similar to that described in Example 57, using glycine (2,2,2-trifluoro)ethyl ester trifluoroacetate instead of glycine benzyl ester p.tosylate. Oily product. Yield: 78%. Rf=0.80 (CHCl$_3$/MeOH/H$_2$O 9:1:Sat.).

EXAMPLE 60

N-[3-Mercapto-2-benzyl-propanoyl]glycine benzylamide

The title compound is obtained by a procedure similar to that described in Example 57, using glycine benzylamide trifluoroacetate instead of glycine benzyl ester p.tosylate. Oily product, which crystallizes slowly. Yield 90%. Rf=0.34 (CHCl$_3$/MeOH/Water 9:1:Sat.).

The results of biological and pharmacological investigations reported below demonstrate the valuable enkephalinase-inhibiting, antalgic and hypotensive properties of the compounds of this invention.

Thus, the present invention includes within its scope a therapeutic composition having particularly enkephalinase-inhibiting, antalgic and hypotensive properties comprising, as active ingredient, a compound of the formula (I) or a pharmaceutically acceptable addition salt thereof with a suitable acid or base.

A—Biological investigation

Determination of the "enkephalinasic" (enkephalin dipeptidylcarboxypeptidasic) activity and determination of the effect of inhibitors.

The enzyme preparation used is a membrane fraction from the striatum of rats or mice.

This fraction is obtained by homogenization at 4° C. in 20 volumes Tris-HCl buffer 0.05M (pH 7.4) followed by two successive centrifugations (1000 g×min. and 200,000 g×min.) at the end of which the sediment of the second centrifugation is retained. It is washed by re-suspension in 10 ml of the buffer followed by centrifugation (200,000 g×min) and the resulting sediment is in turn washed superficially to complete the removal of the soluble enzymes. The resulting membrane fraction is taken up into the buffer at 4° C., to obtain a suspension comprising about 1.5 mg proteins per ml.

An aliquot sample (50 μl) of the membrane suspension is then incubated in a final volume of 100 μl at 25° C. in the presence of 10 nM leucine-enkephalin $^3$H (39 Ci/mmole), previously purified by column chromatography over Porapak Q (100–120 mesh, Waters Assoc.) and 0.1 nM puromycine, an aminopeptidase inhibitor. Incubation time is generally set at 15 mn. in order to determine the initial rate of the formation of tripeptide Tyr-Gly-Gly-$^3$H characteristic of the enkephalin dipeptidylcarboxypeptidasic (enkephalinasic) activity. The reaction is terminated by addition of 25 μl 0.2N HCl and the tripeptide is isolated by column chromatography over Porapak Q or on a thin layer of silica, according to methods described by Malfroy et al. (B. Malfroy, J. P. Swerts, C. Llorens & J. C. Schwartz, Neuro-Science Letters, 11, 329, 1979).

The results obtained with either method have always been consistent.

Determination of the radioactivity of the tripeptide is effected by liquid scintillation spectrometry.

The effect of inhibitors is established by experiments in the presence of increasing concentrations of such materials, which leads to the determination of the 50% inhibitory concentrations calculated by means of data analysis according to the method of Parker and Waud (J. Pharmacol. Exper. Ther., 177, 1, 1971). In some cases the competitive nature of the inhibition was established by incubation experiments in the presence of a fixed concentration of the inhibitor and of increasing concentrations of the substrate.

| Compounds No. | 50% inhibitory concentration |
|---|---|
| 2 | $1.5 \times 10^{-6}$M |
| 5 | $2 \times 10^{-5}$M |
| 27 | $5 \times 10^{-6}$M |
| 28 | $2 \times 10^{-7}$M |

-continued

| Compounds No. | 50% inhibitory concentration |
|---|---|
| 32 | $1 \times 10^{-7}$M |
| 35 | $4 \times 10^{-7}$M |
| 33 | $1 \times 10^{-6}$M |
| 18 | $5 \times 10^{-9}$M |
| 20 | $5 \times 10^{-9}$M |
| 22 | $7 \times 10^{-9}$M |
| 24 | $4 \times 10^{-9}$M |
| 53 | $3.8 \times 10^{-7}$M |
| 54 | $2.6 \times 10^{-7}$M |
| 55 | $3.5 \times 10^{-7}$M |
| 56 | $4 \times 10^{-7}$M |
| 57 | $7.8 \times 10^{-9}$M |
| 60 | $3 \times 10^{-8}$M |

B—Pharmacological investigation

The pharmacological investigation of the abovedescribed products make it possible to demonstrate a specific antalgic, anti-diarrhea and hypotensive effect and a potentiation action of the effects of an enkephalin, D Ala$_2$Met Enkephalin (typically antalgic and hypotensive).

The following pharmacological tests were conducted:

I—Acute Toxicity

Determination of the death rate in mice is observed after a single intravenous administration of increasing dosages of the test compounds.

For all the compounds tested, the LD$_{50}$ is in excess of 100 mg/kg/i.v.

II—Subacute toxicity

Compound 53 was administered for 3 weeks to mice at a dosage of 50 mg/kg 3 times/day (150 mg/day). The animals did not exhibit any change of the weight increase rate or any sign of toxicity with respect to the controls. The weight of the organs, and their anatomic-pathologic examination after sacrificing the animals failed to show any difference with respect to the solvent controls.

On the other hand, in the animals in which a reversibility test was conducted upon termination of the treatment, no sign of tolerance, of habit-forming, and no weaning phenomena could be observed.

III—Antalgic activity

1—Hot-plate test

Licking reflex of mice on a plate heated at 55° C. according to the method of Jacob. and co-workers (Arch. Int. Pharmacodyn. 122, 287–300, 1959: 133, 296–300, 1961).

(a) Potentiation of the antalgic effect of D Ala$_2$Met Enkephalin (α) By the intraventricular route (ivt)

Table I below shows that the effect of a subactive dosage (0.3γ) of D Ala$_2$Met Enkephalin on intra ventricular administration is significantly potentiated (p≦0.05) by compounds 2, 28, 29 and 35, and that this effect is antagonized by Naloxone.

(β) By the intravenous route

On intravenous administration, compound No. 35, at a dosage of 100 mg/kg produces a 100% increase of the licking time, with respect to the animals treated with D Ala$_2$Met Enkephalinase (0.3γ, intraventricular).

TABLE I

Hot plate
Potentiation of the antalgic effect of
D Ala₂Met Enkephalin and Naxolone-induced antagonism % Increase of the licking time with

| Test material | Dosage α/mouse ivt | Number of mice | respect to the animals treated with D Ala₂Met Enkephalin (1) |
|---|---|---|---|
| No. 2 + (1) DAla₂Met Enkephalin | 10 | 6 | 274⊕ |
| No. 29 + (1) DAla₂Met Enkephalin | 10 | 6 | 207⊕ |
| No. 28 + (1) DAla₂Met Enkephalin | 10 | 6 | 400⊕ |
| No. 35 + (1) DAla₂Met Enkephalin | 10 | 10 | 240⊕ |
| No. 35 + (1) DAla₂Met Enkephalin + Naloxone (10 mg/kg s.c.) | 10 | 10 | 18 |

(1) The dosage of D Ala₂Met Enkephalin is 0.3 α/mouse, a dosage which is inactive per se.
⊕P<0.05 Wilcoxon's level test

(b) Specific antalgic effect

By the intravenous route

The Table below shows that compounds 19, 53 and 54 have an antalgic effect in the hot (55° C.) plate test.

| Test compound | ED₅₀ (mg/kg/i.v.) |
|---|---|
| 19 | 30 |
| 53 | 3 |
| 54 | 3 |

2—Test in mice of the withdrawal of the tail immersed in water heated to 48° C. according to the method of Sewell and Spencer (Neuropharmacology—1976—15, p. 683–688).

It is apparent from following Table II that on intravenous administration at a dosage of 100 mg/kg compounds 18 and 20:
exhibit a specific antalgic affect
potentiate most significantly the D Ala₂Met Enkephalin administered 15 minutes later by the intraventricular route at subactive dosages from 10 to 30γ/mouse.

This effect is durable and in excess of 2 hours; it is also noted at a dosage of 30 mg/kg with compound No. 20.

3—Phenylbenzoquinone or "writhing test" according to the method of SIEGMUND and co-workers (Proc. Soc. Expert. Biol. Med. 1957, 95, 729–731).

Compounds 53 and 54, injected at a dosage of 0.7 mg/kg i.v. protect the treated animals from phenylbenzoquinone-induced pain, with a significant difference with respect to the controls, p<0.01.

TABLE II

Tail of the mice
Inherent antalgic effect
Potentiation of the antalgic effect with D Ala₂Met Enkephalin

| Products and dose | Route | Number of mice | Increase reaction time (%) | | | | |
|---|---|---|---|---|---|---|---|
| | | | $20^{mn}$ | $45_{mn}$ | $60^{mn}$ | $90^{mn}$ | $120^{mn}$ |
| N° 18-100 mg/kg | i.v. | 6 | 38 | 80⊕ | 120⊕ | 61⊕ | 90 |
| N° 20-100 mg/kg | i.v. | 6 | 59 | 196⊕ | 150⊕ | 88⊕ | 85 |
| N° 18-100 mg/kg + D Ala₂Met Enkephalin (30 γ ivt) | i.v. | 6 | 0 | 280⊕ | 166⊕ | 87⊕ | 174⊕ |
| N° 20-100 mg/kg + D Ala₂Met EnKephalin (15 γ ivt) | i.v. | 6 | 239⊕⊕ | 528⊕⊕⊕ | 321⊕⊕⊕ | 382⊕⊕⊕ | 322⊕⊕⊕ |
| N° 20-30 mg/kg + D Ala₂MetEnkephalin (15 γ ivt) | i.v. | 6 | 247⊕⊕⊕ | 353⊕⊕⊕ | 283⊕⊕⊕ | 210⊕ | 203⊕ |

⊕ <0.05
⊕⊕ <0.02
⊕⊕⊕ <0.01

(c) Hypotensive activity specific enkephalin-potentiating activity, (LAUBIE M., SCHMITT H., VINCENT M., REMON D. Central cardiovascular effects of Morphinometric peptids in dogs. European Journal of Pharmacology, Vol. 46, 67–71, 1977).

On intravenous administration, compounds 18 and 24 produced a decrease of the blood-pressure from as low a dosage as 0.3 mg/kg.

The results of the above investigations demonstrate the low toxicity and the useful enkephalinase-inhibiting, antalgic and hypotensive properties of the derivatives of this invention which make them applicable in human and veterinary medicine.

The therapeutic composition of this invention may be administered to humans by the oral, parenteral or rectal route.

Each unit dosage contains advantageously 0.5–100 mg active ingredient. The daily dosage regimen may vary from 0.5 mg to 200 mg active ingredient.

What is claimed is:

1. A compound selected from the group consisting of:
N-[(R,S)-3-acetylthio-2-benzyl-propionyl]-glycine methyl ester;
N-[(R,S)-3-mercapto-2-benzyl-propionyl]-glycine;
N-[(R,S)-3-acetylthio-2-benzyl-propionyl]-L-alanine methyl ester;
N-[(R,S)-3-mercapto-2-benzyl-propionyl]-L-alanine;
O-benzyl,N-[(R,S)-3-mercapto-2-benzyl-propionyl]-L-serine;
N-[(R,S)-3-acetylthio-2-benzyl-propionyl]glycine benzyl ester;
N-[(R,S)-3-acetylthio-2-benzyl-propionyl]glycine p.fluorobenzyl ester;
N-[(R,S)-3-acetylthio-2-benzyl-propionyl]glycine 2,2,2-trifluoroethyl ester;
N-[(R,S)-3-acetylthio-2-benzyl-propionyl]glycine benzylamide;
N-[(R,S)-3-mercapto-2-benzyl-propionyl]glycine benzyl ester;

N-[(R,S)-3-mercapto-2-benzyl-propionyl]-glycine 2,2,2-trifluoroethyl ester;

N-[(R,S)-3-phenylacetylthio-2-benzyl-propionyl]-glycine benzyl ester; and

N-[(R,S)-3-benzylthio-2-benzyl-propionyl]-glycine benzyl ester.

2. Therapeutic composition having particularly enkephalinase-inhibiting, antalgic and anti-diarrhea activities, comprising, as active ingredient a therapeutically effective amount of a compound selected from the group consisting of:

N-[(R,S)-3-mercapto-2-benzyl-propionyl]-glycine;

N-[(R,S)-3-mercapto-2-benzyl-propionyl]-L-alanine;

O-benzyl,N-[(R,S)-3-mercapto-2-benzyl-propionyl]-L-serine;

N-[(R,S)-3-acetylthio-2-benzyl-propionyl]glycine benzyl ester;

N-[(R,S)-3-acetylthio-2-benzyl-propionyl]glycine p.fluorobenzyl ester;

N-[(R,S)-3-acetylthio-2-benzyl-propionyl]glycine 2,2,2-trifluoroethyl ester;

N-[(R,S)-3-acetylthio-2-benzyl-propionyl]glycine benzylamide;

N-[(R,S)-3-mercapto-2-benzyl-propionyl]glycine benzyl ester; and

N-[(R,S)-3-mercapto-2-benzyl-propionyl]-glycine 2,2,2-trifluoroethyl ester; in admixture with a therapeutically acceptable excipient.

3. Therapeutic composition as claimed in claim 2, in unit dosage form, each unit dose containing 0.5–100 mg active ingredient.

4.

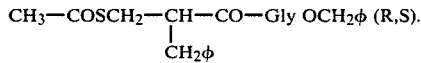

5. Therapeutic composition as claimed in claim 2, wherein said compound is

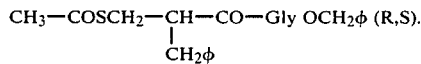

6.

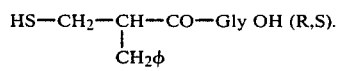

7. Therapeutic composition as claimed in claim 2, wherein said compound is

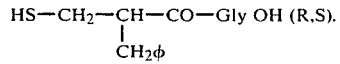

8. Aminoacid derivatives having the following general formula:

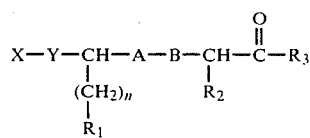

in which:

A is carbonyl;

B is amino;

$R_1$ is selected from phenyl; and phenyl mono- or polyhalosubstituted;

n is 1;

$R_2$ is selected from: hydrogen; methyl and benzyloxymethyl;

$R_3$ is a group selected from —$OR_4$ and —$NHR_4$ in which $R_4$ is selected from: hydrogen; straight- and branched-chain $C_{1-8}$ alkyl; straight and branched-chain $C_{1-8}$ alkyl mono- or poly-halosubstituted; phenyl($C_{1-4}$alkyl); and phenyl($C_{1-4}$alkyl) mono- or polyhalosubstituted on the phenyl group;

Y is —NH— or —$CH_2$—;

X is selected from: $C_{1-2}$alkyl substituted with mercapto; mercapto; aliphatic ($C_{1-4}$acyl)thio; benzoylthio; and phenyl ($C_{1-4}$alkyl) carbonylthio, and their addition salts with pharmaceutically acceptable acids and bases.

9. Compounds according to claim 8, wherein $R_2$ is hydrogen.

10. Therapeutic composition having particularly enkephalinase-inhibiting, antalgic and anti-diarrhea activities, comprising, as active ingredient a therapeutically effective amount of a compound selected from the group consisting of the compounds having the formula:

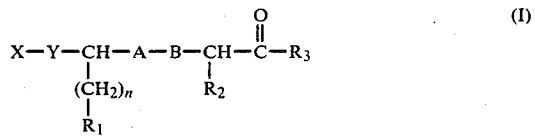

in which:

A is carbonyl;

B is amino;

$R_1$ is selected from phenyl; and phenyl mono- or polyhalosubstituted;

n is 1;

$R_2$ is selected from: hydrogen; methyl; and benzyloxymethyl;

$R_3$ is a group selected from —$OR_4$ and —$NHR_4$ in which $R_4$ is selected from: hydrogen; straight- and branched-chain $C_{1-8}$ alkyl; straight and branched-chain $C_{1-8}$ alkyl mono- or polyhalosubstituted; phenyl($C_{1-4}$alkyl); and phenyl($C_{1-4}$alkyl) mono- or polyhalosubstituted on the phenyl group;

Y is —NH— or —$CH_2$—;

X is selected from: hydrogen; $C_{1-2}$alkyl substituted with mercapto; mercapto; aliphatic ($C_{1-4}$acyl) thio; benzoylthio; and phenyl ($C_{1-4}$alkyl) carbonylthio;

and their addition salts with pharmaceutically acceptable acids and bases, together with a therapeutically acceptable carrier.

11. Aminoacid derivatives having the following general formula:

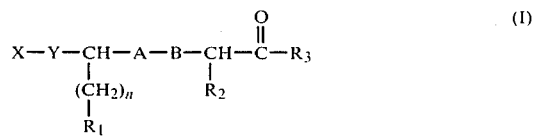

in which:

A is amino;

B is carbonyl;

$R_1$ is selected from phenyl; and phenyl mono- or polyhalosubstituted;

n is 1;

$R_2$ is selected from: hydrogen; straight- and branched $C_{1-6}$alkyl; benzyl; and benzyloxyalkyl;

$R_3$ is a group selected from $-OR_4$ and $-NHR_4$ in which $R_4$ is selected from: hydrogen; straight- and branched-chain $C_{1-8}$alkyl; straight and branched-chain $C_{1-8}$alkyl mono- or poly-halosubstituted; phenyl($C_{1-4}$alkyl); and phenyl($C_{1-4}$alkyl) mono- or polyhalosubstituted on the phenyl group;

Y is a group selected from $-NH-$ or $-CH_2-$;

X is selected from: hydrogen; $C_{1-2}$alkyl substituted with a substituent selected from alkoxycarbonyl, carboxy, mercapto, aliphatic ($C_{1-4}$acyl)thio, and benzoylthio; mercapto; aliphatic ($C_{1-4}$acyl)thio; benzoylthio; and phenyl ($C_{1-4}$alkyl) carbonylthio;

and their addition salts with pharmaceutically acceptable acids and bases.

12. Compounds according to claim 11 wherein $R_2$ is hydrogen.

13. Compounds according to claim 11 wherein Y is NH.

14. Compounds according to claim 11 wherein Y is $CH_2$ and X is SH.

15. Therapeutic composition having particularly enkephalinase-inhibiting, antalgic and anti-diarrhea activities, comprising, as active ingredient a therapeutically effective amount of a compound according to claim 11, together with a therapeutically acceptable carrier.

16. A compound as claimed in claim 1, which is N-[(R,S)-3-mercapto-2-benzyl-propionyl]-glycine.

17. A compound according to claim 1, which is N-[(R,S)-3-mercapto-2-benzyl-propionyl]-L-alanine.

* * * * *